US010092195B2

(12) United States Patent
Lovoi et al.

(10) Patent No.: US 10,092,195 B2
(45) Date of Patent: *Oct. 9, 2018

(54) NONINVASIVE DETECTION OF HUMAN BRAIN CONDITIONS AND ANOMALIES

(71) Applicant: Jan Medical Inc., Mountain View, CA (US)

(72) Inventors: Paul A. Lovoi, Saratoga, CA (US); Ray Schumacher, La Jolla, CA (US); Charlie MacVean, San Diego, CA (US)

(73) Assignee: JAN MEDICAL, INC., Munich (DE)

( * ) Notice: Subject to any disclaimer, the term of this patent is extended or adjusted under 35 U.S.C. 154(b) by 653 days.

This patent is subject to a terminal disclaimer.

(21) Appl. No.: 14/565,337

(22) Filed: Dec. 9, 2014

(65) Prior Publication Data

US 2016/0081608 A1    Mar. 24, 2016

Related U.S. Application Data

(63) Continuation-in-part of application No. 11/894,052, filed on Aug. 17, 2007, now Pat. No. 8,905,932.

(Continued)

(51) Int. Cl.
*A61B 5/024* (2006.01)
*A61B 5/00* (2006.01)
(Continued)

(52) U.S. Cl.
CPC ............ *A61B 5/024* (2013.01); *A61B 5/0205* (2013.01); *A61B 5/02007* (2013.01);
(Continued)

(58) Field of Classification Search
CPC . A61B 5/02007; A61B 5/0205; A61B 5/4064; A61B 5/4076; A61B 5/6814;
(Continued)

(56) References Cited

U.S. PATENT DOCUMENTS 4,008,711 A    2/1977  Olinger et al.
4,226,248 A    10/1980 Manoli
(Continued)

FOREIGN PATENT DOCUMENTS

EP    0770352    5/1997

OTHER PUBLICATIONS

Memsic (Accelerometer spec sheet, http://search.alkon.net/cgi-bin/pdf.pl?pdfname=memsic/mxa6500ep.pdf, Mar. 22, 2005).*

(Continued)

*Primary Examiner* — Amelie R Gillman
*Assistant Examiner* — Carolyn Pehlke
(74) *Attorney, Agent, or Firm* — Jan Medical, Inc.

(57) ABSTRACT

Vascular conditions are detected non-invasively in the human body using a collection of information from small local regions of the vasculature, or from a specific signature or "BrainPulse" that can be derived from a patient's heartbeat-induced cranium movements. An array of accelerometers or other sensors are engaged against the head of a patient and skull movements, preferably under 100 Hz, are recorded. Vibration signatures of vessel structures such as branches, aneurysms, stenosis, etc. using random, periodic, band limited or transient analysis provides a library for further processing. The signature library is used to localize the origin of the recognized vascular feature, and the localized feature is presented to the physician in a clinically relevant manner.

23 Claims, 16 Drawing Sheets

Related U.S. Application Data

(60) Provisional application No. 60/838,624, filed on Aug. 17, 2006.

(51) Int. Cl.

| | | |
|---|---|---|
| *G16H 50/20* | (2018.01) | |
| *G16H 50/70* | (2018.01) | |
| *G16H 50/50* | (2018.01) | |
| *A61B 5/02* | (2006.01) | |
| *A61B 7/04* | (2006.01) | |
| *A61B 5/0205* | (2006.01) | |
| *G06F 19/00* | (2018.01) | |
| *G06K 9/00* | (2006.01) | |

(52) U.S. Cl.
CPC .......... *A61B 5/4064* (2013.01); *A61B 5/4076* (2013.01); *A61B 5/6814* (2013.01); *A61B 5/7282* (2013.01); *A61B 7/04* (2013.01); *G06F 19/324* (2013.01); *G06K 9/0055* (2013.01); *G16H 50/20* (2018.01); *G16H 50/50* (2018.01); *G16H 50/70* (2018.01); *A61B 5/7246* (2013.01); *A61B 5/7257* (2013.01); *A61B 5/7267* (2013.01); *A61B 2562/0219* (2013.01)

(58) Field of Classification Search
CPC ......... A61B 5/7267; A61B 7/04; A45C 11/38; A45C 13/126; F16D 3/16; F16D 3/2055; F16D 3/43; G06F 19/324; G06F 19/3437; G06F 19/3443; G06F 19/345; G06K 9/0055
See application file for complete search history.

(56) References Cited

U.S. PATENT DOCUMENTS

| | | | |
|---|---|---|---|
| 4,561,447 A | 12/1985 | Kawamura et al. | |
| 4,928,705 A | 5/1990 | Sekhar et al. | |
| 5,074,310 A * | 12/1991 | Mick ............... | A61B 5/031 600/561 |
| 5,117,835 A * | 6/1992 | Mick ............... | A61B 5/0051 600/561 |
| 5,137,029 A | 8/1992 | Parra | |
| 5,301,679 A | 4/1994 | Taylor | |
| 5,388,583 A | 2/1995 | Ragauskas et al. | |
| 6,024,701 A | 2/2000 | Almog | |
| 6,050,950 A | 4/2000 | Mohler | |
| 6,385,474 B1 | 5/2002 | Rather et al. | |
| 6,887,199 B2 | 5/2005 | Bridger et al. | |
| 7,037,267 B1 | 5/2006 | Lipson | |
| 8,905,932 B2 * | 12/2014 | Lovoi ............... | A61B 5/02007 600/438 |
| 2002/0040189 A1 | 4/2002 | Averkiou et al. | |
| 2002/0067107 A1 | 6/2002 | Lewis | |
| 2002/0077567 A1 | 6/2002 | Mcleod | |
| 2002/0183642 A1 | 12/2002 | Murphy | |
| 2002/0198469 A1 | 12/2002 | Bridger | |
| 2004/0028275 A1 | 2/2004 | Arora et al. | |
| 2004/0249293 A1 | 12/2004 | Sandler et al. | |
| 2005/0234309 A1 | 10/2005 | Klapper | |
| 2006/0100530 A1 | 5/2006 | Kliot | |
| 2006/0161218 A1 | 7/2006 | Danilov | |
| 2009/0012430 A1 | 1/2009 | Lovoi | |
| 2011/0112426 A1 | 5/2011 | Causevic | |
| 2012/0041330 A1 | 2/2012 | Prichep | |
| 2012/0215081 A1 | 8/2012 | Euliano | |
| 2013/0267858 A1 | 10/2013 | Berkow et al. | |
| 2014/0249400 A1 | 9/2014 | Wyeth | |

OTHER PUBLICATIONS

Guevara, Miguel Angel, and Maria Corsi-Cabrera. "EEG coherence or EEG correlation?." International Journal of Psychophysiology 23.3 (1996): 145-153.*

Kurtz, Kenneth J. "Bruits and hums of the head and neck." (1990).*

Jervis, B. W., L. Smaglo, and S. Djebali. "The rapid classification of brain conditions using neural networks." (2001): 4-4.*

United States Patent Office, International Searching Authority, International Search Report and Written Opinion dated May 19, 2016 for International Patent Application No. PCT/US2015/064840, 14 Pages.

United States Patent Office, International Searching Authority, International Search Report and Written Opinion for International Patent Application No. PCT/US2016/040543 dated Sep. 22, 2016, 9 Pages.

Kosugi et al., "Detection and Analysis of Cranial Bruit", IEEE Transactions on Biomedical Engineering, 34(3): 185-192, Mar. 1987.

Kosugi et al., "Sonic Detection of Intracranial Aneurysm and AVM", Stroke, vol. 14, No. 1, pp. 37-42, 1983.

Ferguson, G., "Direct Measurement of Mean and Pulsatile Blood Pressure at Operation in Human Intracranial Saccular Aneurysms", J. Neurosurg., vol. 36, pp. 560-563, 1972.

* cited by examiner

| SENSOR | $\Delta_t$ |
|---|---|
| $S_1$ | $\Delta_{t_1}$ |
| $S_2$ | $\Delta_{t_2}$ |
| $S_3$ | $\Delta_{t_3}$ |

|   | $S_1$ | $S_2$ | $S_3$ | $S_4$ | I |
|---|---|---|---|---|---|
| A | 10 | 25 | 50 | 54 | 1 |
| B | 15 | 24 | 47 | 51 | 5 |
| C | 18 | 22 | 44 | 46 | 10 |
| D | 24 | 23 | 39 | 42 | 5 |
| E | 28 | 24 | 35 | 36 | 1 |

NONINVASIVE DETECTION OF HUMAN BRAIN CONDITIONS AND ANOMALIES

CLAIM OF PRIORITY

This application is a continuation-in-part of application Ser. No. 11/894,052, filed Aug. 17, 2007, now U.S. Pat. No. 8,905,932, which was a regular filing from provisional application No. 60/838,624, filed Aug. 17, 2006.

BACKGROUND OF THE INVENTION

The invention concerns detection of conditions of human vasculature non-invasively, from outside the body, and in particular, locating aneurysms, partial or complete stenoses, ruptures, peripheral bleeding and other abnormal conditions pertaining to the cerebral vasculature, profiling blood or other fluid flow through or around the cerebral vasculature and mapping based on gathered data to provide a spatially resolved characterization of the major vasculature within the head. The system and method of the invention are also useful to detect vascular conditions in other parts of the body, especially the limbs and areas of other major vessels.

Stroke is a manifestation of injury to the brain which is commonly secondary to atherosclerosis or hypertension, and is the third leading cause of death in the United States. Stroke can be categorized into two types, ischemic stroke and hemorrhagic stroke. Additionally, a patient may experience transient ischemic attacks, which are in turn a high risk factor for the future development of a more severe episode.

Examples of ischemic stroke encompass thrombotic, embolic, lacunar and hypo-perfusion types of strokes. Thrombi are occlusions of the arteries created in situ within the brain, while emboli are occlusions caused by material from a distant source, such as the heart and major vessels, often dislodged due to myocardial infarct or atrial fibrillation or carotid disease or surgical or percutaneous intervention. Thrombi or emboli can result from atherosclerosis or other disorders, for example, arteritis and lead to physical obstruction of arterial blood supply to the brain. Lacunar stroke refers to an infarct within non-cortical regions of the brain. Hypo-perfusion embodies diffuse injury caused by non-localized cerebral ischemia secondary to low cerebral perfusion, typically caused by myocardial infarction, arrhythmia, blood loss or prolonged low blood pressure.

Hemorrhagic stroke is caused by intra cerebral or subarachnoid hemorrhage, i.e., bleeding in to brain tissue, following blood vessel rupture within the brain or venous thrombosis. Intra cerebral and subarachnoid hemorrhages are subsets of a broader category of hemorrhage referred to as intracranial hemorrhage.

Intra cerebral hemorrhage is typical due to chronic hypertension and a resulting rupture of an arteriosclerotic vessel. Stroke-associated symptom(s) of intra cerebral hemorrhage are abrupt, with the onset of headache and steadily increasing neurological deficits. Nausea, vomiting, delirium, paralysis, seizures and loss of consciousness are additional common stroke-associated symptoms.

In contrast, most subarachnoid hemorrhage is caused by head trauma or aneurysm rupture that is accompanied by high-pressure blood release that also causes direct cellular trauma. Prior to rupture, aneurysms may be asymptomatic, or occasionally associated with headaches. However, headache typically becomes acute and severe upon rupture and may be accompanied by varying degrees of neurological deficit, vomiting, dizziness, and altered pulse and respiratory rates, photophobia and severe headache and or neck stiffness.

Current diagnostic methods for stroke include costly and time-consuming procedures such as non-contrast computed tomography (CT) scans, electrocardiogram, magnetic resonance imaging (MRI) and angiography. Determining the immediate cause of stroke is difficult. CT scans can detect parenchymal bleeding greater than 5 mm and 95% of all subarachnoid hemorrhages. CT scans often cannot detect ischemic strokes until 6 hours from onset, depending on infarct size. CT only identifies 48% of acute strokes in the first 48 hours. MRI may be more effective than CT scan in early detection of ischemic from hemorrhagic stroke. Advanced imaging systems are not widely available at present and are limited to major hospital centers. Angiography is a definitive test to identify stenosis or occlusion of large and small cranial blood vessels, and can locate the cause of subarachnoid hemorrhages, define aneurysms, and detect cerebral vasospasm. It is, however, an invasive procedure and is also limited by cost and availability.

Immediate diagnosis and care of patients experiencing stroke can be critical. For example, tissue plasminogen activator (tPA) given within three hours of symptom onset in ischemic stroke is beneficial for selected acute stroke patients. In contrast, thrombolytics and anticoagulants are strongly contraindicated in hemorrhagic strokes. Thus early differentiation of ischemic events from hemorrhagic events is imperative. Moreover, delays in confirmation of stoke diagnosis and identification of stroke type limit the number of patients that may benefit from early intervention therapy. In addition, continuous monitoring of stroke patients is not possible with CT or MRI scanners, thus only one snapshot in time is available for diagnosis and treatment. Clinical observations are the basic tool that is used to monitor the progress of stroke patients.

Early detection of an aneurysm is beneficial as it can frequently be treated either by a surgical procedure of clip occlusion or by endovascular coil embolism. Presently, approximately three quarters of patients are treated with clip occlusion, the remainder with endovascular coil embolism. Either surgery, particularly the endovascular procedure, can by performed with low complication rate and high rate of success.

Once an aneurysm ruptures, however, the patient declines rapidly due to major brain injury, and over 50% of aneurysm rupture patients die acutely. Thus detection of at risk aneurysms is of great benefit. A physician faced with possible aneurysm warning signs must judge whether the symptoms warrant the trauma, expense and morbidity of contrast angiography.

Ferguson, in J. Neurosurg. 36:560-563 (1972), suggested detecting aneurismal signals by recording sounds from aneurysms exposed at operations using a cardiac phono-catheter. Kosugi et al., in Stroke 14 (1) 37-42 (1983), disclosed the use of a "cement wall microphone", (contact accelerometer) in contact with the cranium and the teeth in an attempt to detect aneurysms.

Despite these known devices, there remains a need for a detector that is designed to more effectively record, analyze, localize and present, in a clinically useful manner, cerebral arterial and venous conditions. Devices and methods to date have not localized the detected vascular conditions and do not present the collected data in a clinically useful way.

SUMMARY OF THE INVENTION

The current invention is a system and method for detecting a vascular condition non-invasively in the human body, by a collection of signal information received from local, small regions of the vasculature. This is accomplished in a preferred embodiment by attaching, or contacting, an array of accelerometers or other sensors, to or against the head, and/or other points of interest, to a patient and recording signals.

The vibration signatures of blood vessel structures such as branches, aneurysms, stenoses, vasospasms or other structures using random, periodic, band limited or transient analysis provides a library for further processing. The library becomes part of a cerebral modeling arithmetic computer using basis functions, or other artificial neural network. The developed signature library is then used to facilitate localizing the origin of the recognized vascular feature; the localized feature is then presented to the physician in a clinically relevant manner.

The data to build the neural network (NN) and/or data store for correlation are obtained by acquiring data from patients with known pathologies as well as controls, and optionally with studies of constructed or cadaver vasculatures. The data are formatted according to the requirements of each processing method before being used for training or algorithm construction.

These and other objects, advantages and features of the invention will be apparent from the following description of a preferred embodiment, considered along with the accompanying drawings.

DESCRIPTION OF PREFERRED EMBODIMENTS

General Outline of Process

Figure 1A:
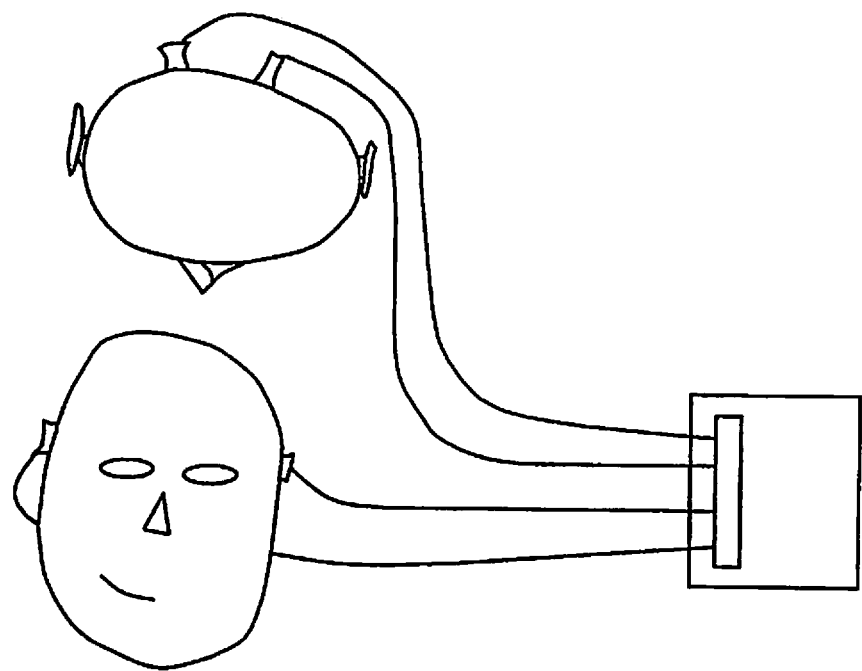
FIG. 1A is a plan and elevation view of sensors on a head.

Periodic pulses from the heart produce waves of expanding blood vessels within the body. The tissue surrounding the blood vessels is displaced during the pulse and contracts again after the pulse. This displacement propagates outward from the blood vessel. In the case of the brain, this displacement reaches the skull and displaces the bone in response the displacement of the blood vessel wall. Extremely sensitive accelerometers record this displacement.

The character of the signal recorded by the accelerometers is dependent on the nature of the displacement caused by the blood pulse. At a restriction in the vessel the displacement before the restriction is larger than it would be without the restriction and the displacement beyond the restriction is less. The spatial distribution of displacement produces a different signature than that recorded by an unrestricted vessel. Likewise an aneurysm allows a circulation of blood within the bulb of the aneurysm during the pulse and produces a periodic signal that modifies the displacement signal. Other geometric arrangements of vessels likewise produce unique signatures in displacement.

The accelerometers are very sensitive, typically 500 mV/g or more. Such an accelerometer is a model from Dytran, of California.

Limitations of Acoustic Signal Detectors

Accelerometers have a distinct advantage over microphones since microphones require acoustic signals to propagate through the soft tissue of the brain, conduct through the hard bone of the skull, again transfer to the soft tissue of the skin and finally be transferred to the microphone. Such devices have been most successful when attached to the teeth, positioned within the ear or focused on the eye sockets. Thus the use of microphones has been more successful when they can either have direct bone contact or look where there is no skull present. Accelerometers measure the displacement of the entire structure.

Elimination of External Sources of Signal

The microphone is also very sensitive to sound signals produced from outside the body, such as sirens, talking, doors slamming and other sound signals. Accelerometers are much less sensitive to acoustic signals and generally are only sensitive to signals along the primary axis of the detector.

Localization with Phase

The use of multiple accelerometers positioned around the head allows signals from different parts of the brain to be distinguished by location. Beyond just the relative magnitude of the signals from each of the sensors the phase relationship of the signals between sensors is used to determine the location of the displacement source. Since there are a multitude of signals produced during the pulse from different spatial positions and with the pulse traveling from the proximal to distal portions of the vasculature, a means to distinguish each of these signals is needed. This differentiation is accomplished by using a priori information about the head and the approximate positions of each of the accelerometers. For example signals cannot emanate from locations outside of the head nor at times that are not related to the blood pulse.

Timing for Localization

A gating sensor, an EKG electrode, is used to provide timing information to the system. Since the heart rate varies in a given person both at rest and with exertion, the timing signal is used as an approximate starting point for timing the signal arrival at the sensors but cannot determine the pulse timing. Leeway is still needed as the intra pulse timing may be increasing or decreasing for each pulse.

Localization Example

Signals data are captured from multiple sensors during a pulse. The signals from the multiple sensors are shifted in time by a guessed amount and then added together. The resulting signal is then analyzed either by direct amplitude, by Fourier transform or by another algorithms. This process is continued over the valid range of phases from each sensor. If a given signal is correlated with the signal from another sensor then the resulting combined signal will have an enhanced signature when the phases represent the location of the signal and not for surrounding phases within the allowable phase space.

The quality of a signature can be quantified and that quantification can be established for each phase shift between sensors. As the phase is shifted over the possible range the figure of merit (quantified result of a single phase relationship) will increase and decrease. The peaks represent recognized signatures at localized positions. While this process is straightforward it is very processor intensive. The allowable phase shifts for all the sensors can be calculated beforehand and this range used to limit the correlation space. The computational problem can be parsed such that parallel processors tackle the problem in parallel thus reducing the time from data collection to data presentation.

It is important to note that once the initial data has been analyzed the relative phase between sensor data for the many signals within the brain is known, continued analysis of captured data is much less computational intensive. This a priori knowledge vastly reduces the computational requirements of the system and allows near real time presentation of the data. Current computers are certainly capable of completing the vast amount of computations in times suitable for clinical use and this will just improve as the speed and processing throughput of computers increases.

Creation of Synthetic Image

The data needs to be presented in a recognized manner for the clinician to make use of it. By the nature of the data capture and processing, the most prominent structures are most readily identified and localized. This is not a complete map of the brain vasculature. Using a priori knowledge of the typical structure of the vasculature (and noting that there are significant deviations from the "typical" structure) the identified structures can be placed onto a cartoon of the entire vasculature, replacing the typical cartoon representations with improved representations based on the data analysis. This synthetic image is then presented to the clinician; as a 3D representation, a simulated CT or MRI scan or as an angiogram. As data continues to be acquired and processed the synthetic image can be updated.

Ultrasound Bubbles

Ultrasound contrast agents are materials that can be injected as an IV to improve the imaging of blood vessels by ultrasound. The contrast consists of very fine particles and a method of attaching very small bubbles to the particle. To avoid any associated problems with embolisms the particle and bubbles together are smaller than a typical red blood cell thus allowing the bubbles to pass through from the arteries to the veins. These bubbles are also engineered to not join together as they are formed about a tiny particle rather than free standing bubbles that might have a tendency to enlarge by combining.

The purpose of injecting bubbles into the vasculature is to increase the ultrasonic contrast of the blood by adding well dispersed low density material. Contrast agent is rapidly eliminated in the blood by the breaking of the newly formed bubbles.

An unrecognized feature of the contrast agents is that as each bubble breaks it creates a disturbance within the vasculature which is highly localized. Ultrasound contrast media are already FDA cleared for use in stroke diagnostics and vessel imaging. To ensure the safety of injecting bubbles into the blood the bubble size is very well controlled.

Bubbles of the same size have a well-defined and distinctive signature when they break. This consistency allows for precise localization of the resulting signal. Since the bubbles are smaller than a red blood cell, the bubbles are able to perfuse from the arteries to the veins. The bubbles break randomly over a controlled period of time, typically five to 20 minutes after injection. If the amount of contrast media that is injected is reduced significantly from the amount typically given for ultrasound imaging the number of bubbles that break can be controlled to have, on average, a few milliseconds between bursts. Thus a system that is sensing the breaks from multiple sensors can localize the position of the bubble when it broke to a few mm or better resolution. Summing over a large number of events will produce a 3D map of where the bubbles have reached.

One of the major objectives of stroke treatment is determining whether a patient has a stroke at all and if they have had a stroke to differentiate an ischemic from a hemorrhagic. This differentiation is critical to caring for the patient. If clot dissolving drugs are used on a hemorrhagic patient the likely outcome is significantly worse, including death, over no treatment at all. Likewise not treating an ischemic stroke patient within the first four and one-half hours (for current drugs) of the stroke results in no treatment at all.

A 3D bubble map will show areas that are not perfused, an area with little or no bubbles showing up; the signature of a vessel blockage or ischemic stroke. Aneurysms, the typical cause of hemorrhagic strokes, will show up in both the direct sensor signals and in the 3D bubble map. A lack of perfusion in an area around the aneurysms would be a strong indicator of non-flowing pooled blood. A perfused area distal to the aneurysm would be a further indication of no ischemic stroke. Thus the system would allow rapid, clinically relevant, differentiation of stroke type enabling treatment to be delivered in a timely manner.

Merger of Data

The sensors deliver data on major unusual events in the vasculature. Merging this data into a "typical" 3D map of the complete vasculature ignores the real differences between individuals. It still provides clinically relevant data, such as lack of blood flow in an area of the brain and then a subsequently reperfusion of that area. This highlights the major advantage of having a continuous monitoring system over a snapshot monitoring such as CT, MRI or contrast angiography. Adding the bubble map would allow a complete map of the vasculature since the bubbles burst through out all the perfused vessels within the brain. Since the same sensors, and sensor locations, are used to produce both maps, the two data sets can be merged to form a single complete map of the vasculature. In addition, this data set can be merged with the CT scan or other scans to combine the data from each to provide the clinician a better picture of the patient's condition.

Neural Network

The array of different accelerometer signatures produced by features within the vasculature is quite large due to the variable physiology of patients but there are generally only a few major underlying features. This type of data is ideal for using neural networks to identify the features causing the signature to be categorized. As the library of unique features and the associated signatures grows the neural network will improve in correctly identifying features in patients. Neural networks typically are trained by inputting a set of known inputs and known outputs and allowing the weights of the neural connections to change to optimize the matching of the inputs and outputs. When a new input is presented to the neural network the output closest to the input is given the highest output even if the input is not a perfect match to any of the training set.

Beam Forming

In a process similar to localization previously discussed, beam forming varies the phase between data produced by different sensors. It is the purpose of beam forming to systematically vary the phase and retain the resulting signal. With small steps in the phase a very high spatial resolution map of the vasculature is produced. Beam forming is used when a feature of interest is localized and more detailed information is desired about that feature. Beam forming is computational intensive but lends itself to parallel processing and will be aided by improvements in processing power of both general purpose and special purpose processors.

In the drawings, FIG. 1A shows a patient with sensors attached to various places on the head. The sensors are connected by cables, but could be connected wirelessly, to the analysis portion of the system.

Figure 1B:
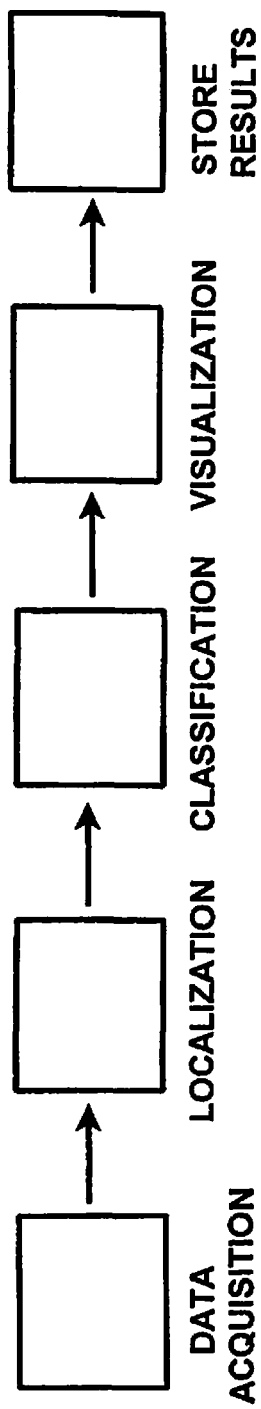
FIG. 1B is a block diagram of the steps of the invention.

FIG. 1B shows a block diagram of the analysis and visualization portion of the system. The signal arrives from each sensor and is conditioned and processed in the data processing block. The processed signal is digitized and processed in parallel. The processors analyze the signal for matches to library conditions and identify matches that are then used with multiple sensors to localize the source of the matched signal. This process is repeated for each identified signal for multiple locations. The collection of all the localized and identified data is processed by the image database for presentation. The digitized input signal is also stored in the array data memory for further analysis. Localized features can be further characterized by using beam forming techniques. In the beam forming mode multiple sensors are used to "look" at the same location and the resulting signals analyzed for additional information. Beam forming can be used to shift or scan the region of interest to further characterized and localize the feature.

Figure 35:
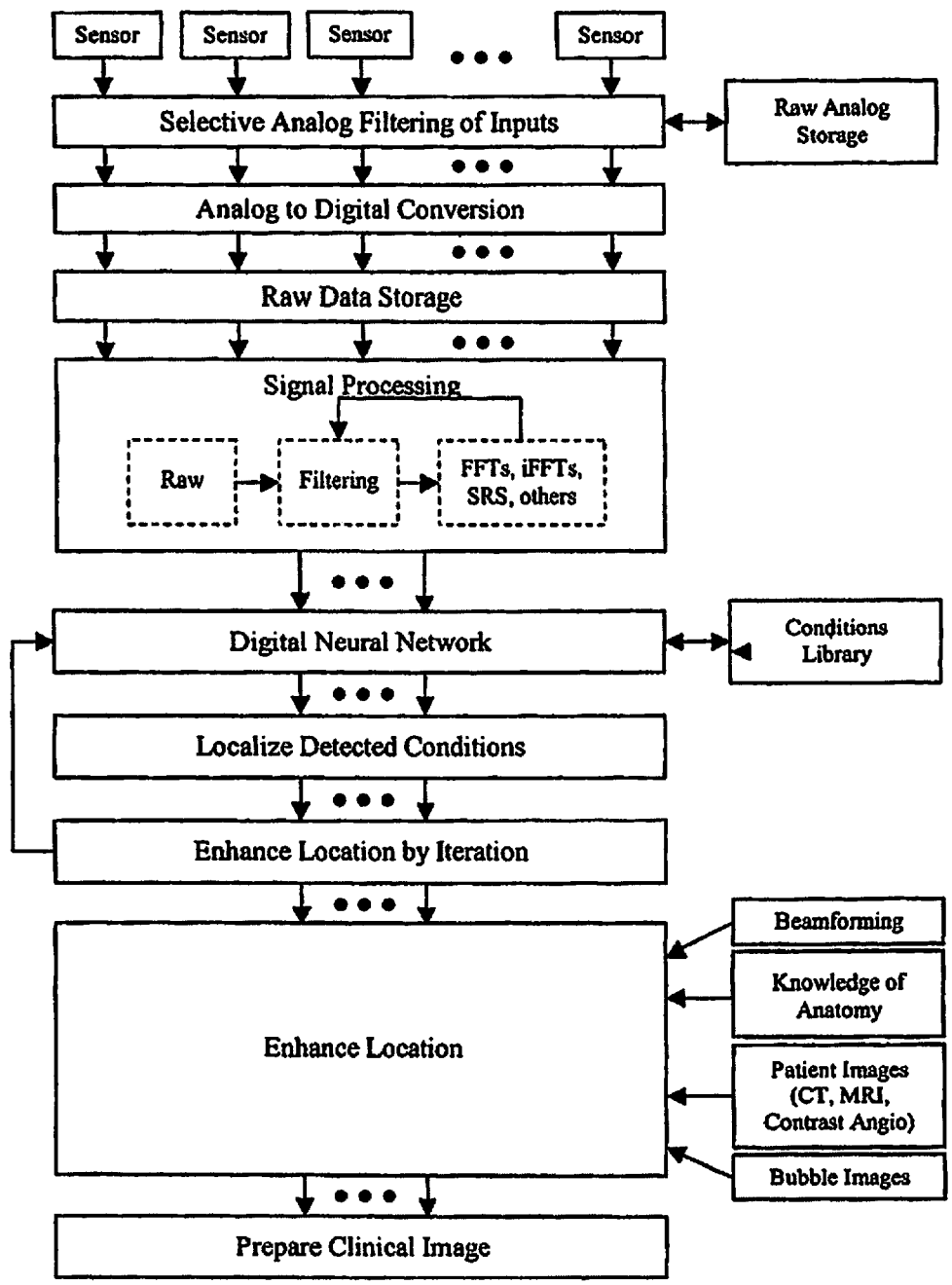
FIG. 35 is a flow diagram outlining the overall system.

Some of the features of the system as represented in FIG. 35 are:

The use of noise cancellation.
The elimination of overriding signals.
The localizers for each signal type.
The use of the raw data memory.
The causal network.
The patient factors input and how it is used.
The image database.
The image.
The dynamic filtering and its purpose.

Figure 2:
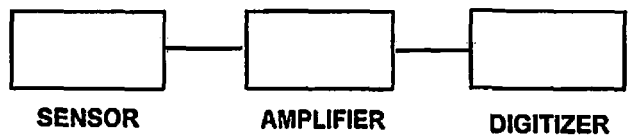
FIG. 2 is a block diagram of the sensor processing steps.

FIG. 2 is a more detailed block of the sensor and data acquisition block in FIGS. 1A and 1B. The sensor signal is amplified and possibly filtered, sometimes dynamically, before being amplified and finally digitized. The signal from each of the sensors in FIG. 1A are digitized maintaining the time relationship between each sensor.

Figure 3:
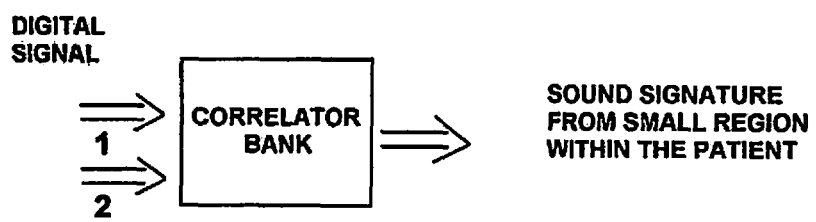
FIG. 3 is a diagram of the correlation circuit.

FIG. 3 shows a block diagram of the correlator bank that localizes the signals. All the sensor signals, with their timing information, are fed into to the correlator bank. The correlator determines, by changing the time relationship between different sensor signals, when two signals are from the same source and record those time relationships. Multipath rejection via modeling of the signal phase delay of the skull (or body) may be used to improve accuracy of the algorithms. The relative attenuation of the intervening materials may also be used. The signal that is common to the multiple sensor signals is recorded as the signal that was created at the location that is determined by the time differences between the arrival of the signal at each sensor, as will be further explained below.

Figure 4:
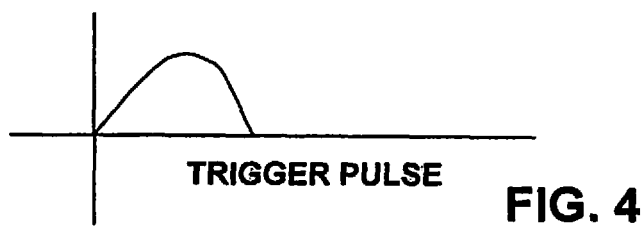
FIG. 4 is a diagram of a trigger pulse amplitude VS time.
Figure 5:
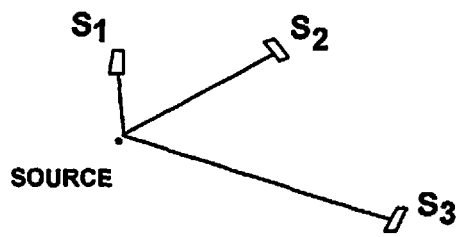
FIG. 5 is a diagram of sensors at various distances from a pulse source.
Figure 6:
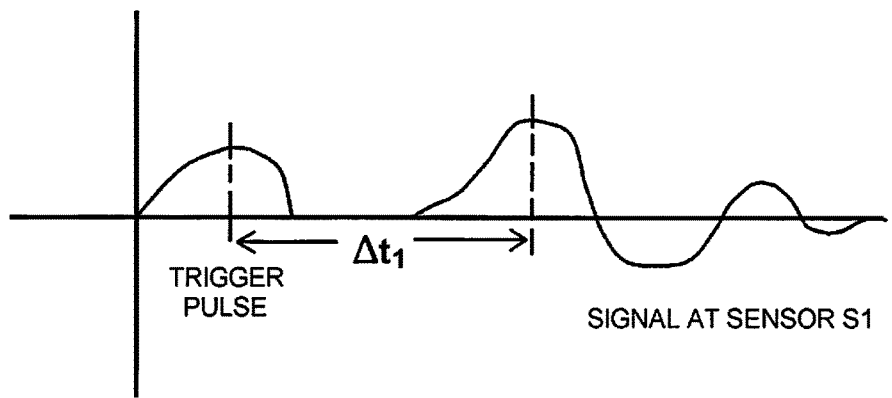
FIG. 6 is a diagram of a trigger pulse and a received pulse at a distant sensor.
Figure 7:
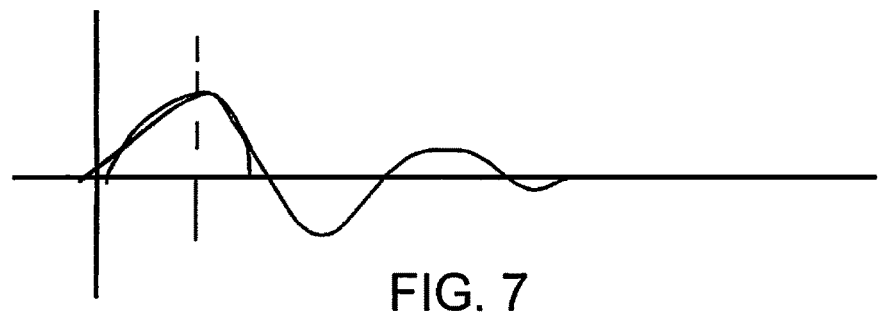
FIG. 7 is the overlay of the trigger pulse and the received pulse shifted by time delta t1.
Figure 8:
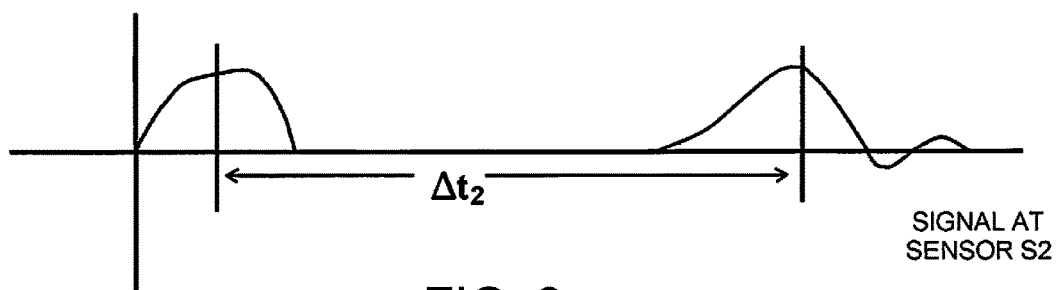
FIG. 8 is a diagram of a trigger pulse and a received pulse from a further sensor.
Figures 9, 10:
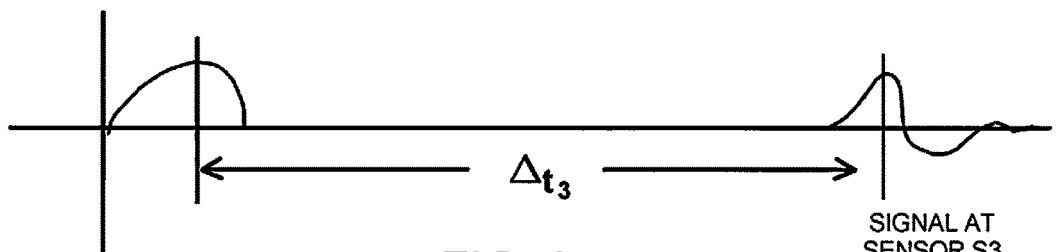
FIG. 9 is a diagram of a trigger pulse and a received pulse from the furthest sensor.
FIG. 10 is a table the time of first signal arrival from the trigger pulse for each sensor.

FIG. 4 shows a simple trigger pulse test source signal in amplitude versus time. FIG. 5 shows a diagram of the location of a signal source and three sensors, S1, S2 and S3, shown at different distances from the signal source. FIG. 6 shows a time vs. amplitude waveform of the trigger pulse and the arrival of the signal at sensor S1. The time that the signal takes to arrive at sensor S1 is delta t1. FIG. 7 shows the superposition of the two signals in FIG. 6 translated in time by delta t1. FIG. 8 shows the same data as FIG. 6 but for sensor S2 that is farther from the source than sensor S1. The time for the signal to arrive from the source at sensor S2 is delta t2. FIG. 9 shows that same data as FIGS. 6 and 8 but for sensor S3 with a transit time of delta t3. FIG. 10 is a table with the arrival time for the signal for each of the sensors, S1, S2 and S3.

Figure 11:
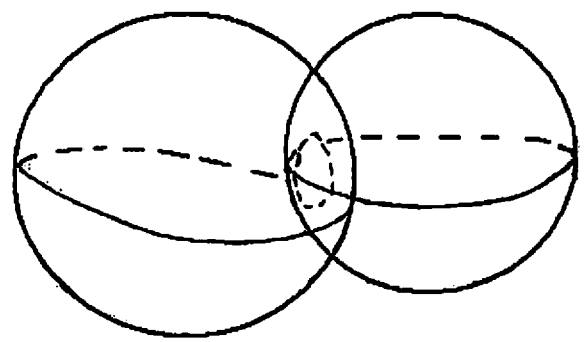
FIG. 11 is a diagram of two intersecting spheres of different diameters.
Figure 12:
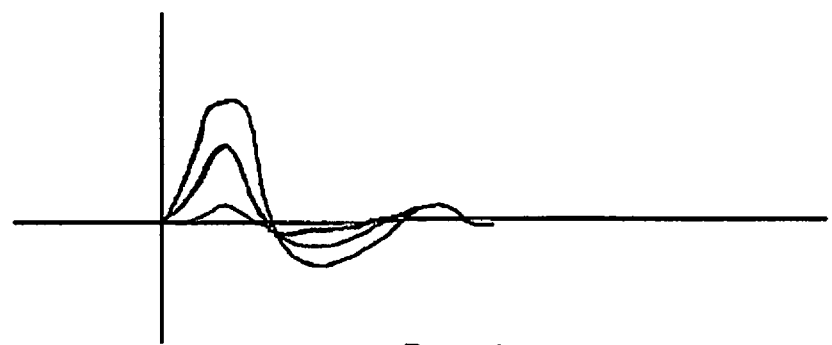
FIG. 12 is a diagram of three sensor signals shifted according to the table in FIG. 10.
Figure 13:
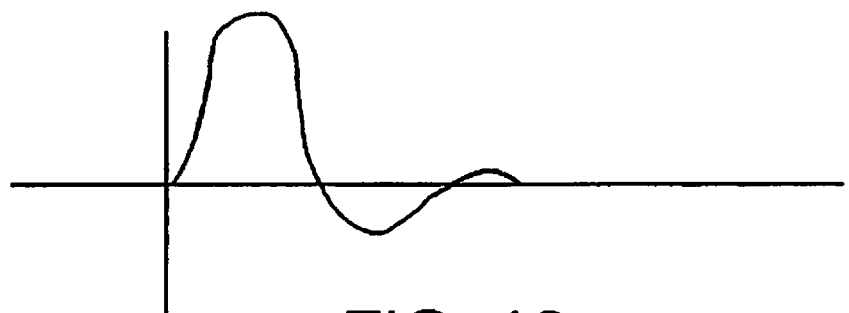
FIG. 13 is a diagram of the sum of the three sensor signals in FIG. 12.

FIG. 11 shows two different radius intersecting spheres with the dotted line showing the locus of points where the distance between the centers of sphere 1 and sphere 2 are constant. This locus of points represents the possible position of the source based on only the signal from two sensors. Adding a third sensor, not shown, would restrict the location of the source to a single location, thus fixing its location with respect to the three sensors. FIG. 12 shows all the sensor signals from FIGS. 6, 8 and 9 translated by the times listed in FIG. 10. FIG. 13 shows the sum of the three signals shown in FIG. 12.

Figure 14:
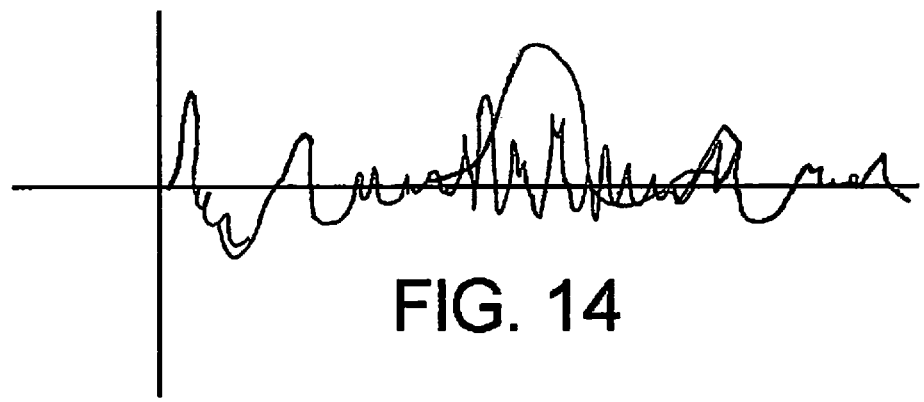
FIG. 14 is a received sensor signal as shown in FIG. 6 and typical noise signal.
Figure 15:
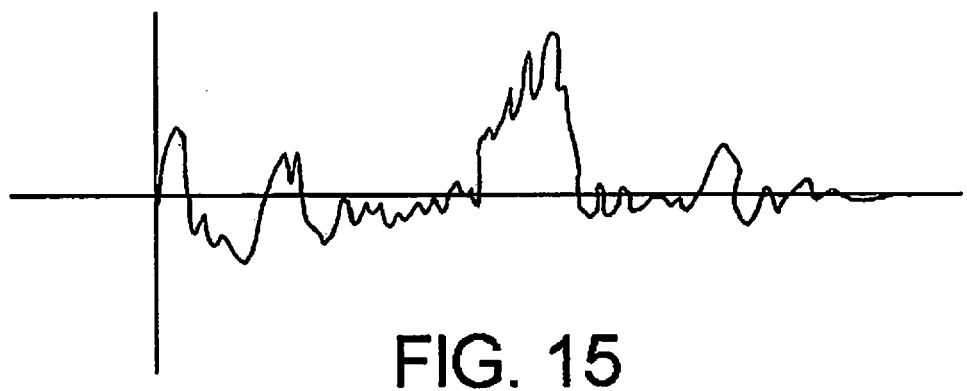
FIG. 15 is a diagram of the sum of the noise signal and the signal from sensor 1.
Figure 16:
FIG. 16 is a diagram of the sum of noise signal and the signal from sensor 2.
Figure 17:
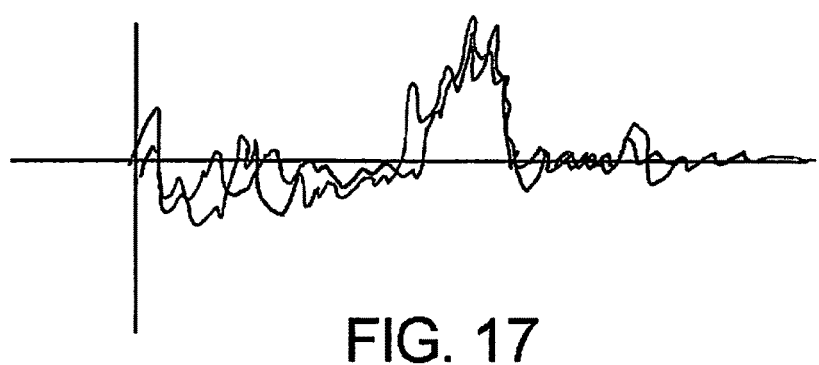
FIG. 17 is a diagram of the superposition of the noise signals from each of the three sensors.
Figure 18:
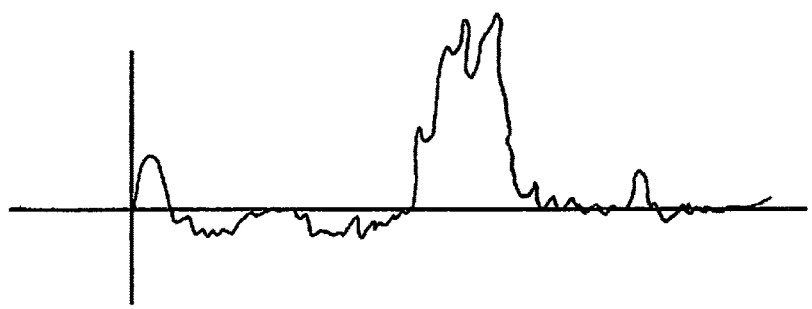
FIG. 18 is a diagram of the sum of the noise signals from each of the three sensors.

FIG. 14 shows the typical signal noise that might be expected to be present on the sensor signal along with the sensor signal as shown in FIG. 6. FIG. 15 shows how the sensor signal in FIG. 14 would look for a typical signal noise environment. FIG. 16 shows the same signal as FIG. 15 but for sensor S2 rather than sensor S1. FIG. 17 shows superposition of the noisy signals from all the sensors, translated by the times shown in the table in FIG. 10. FIG. 18 shows the sum of all the signals in FIG. 17 with the noise reduced due to the summing of random noise and the signal increased by the superposition of the common signal.

Figure 19A:
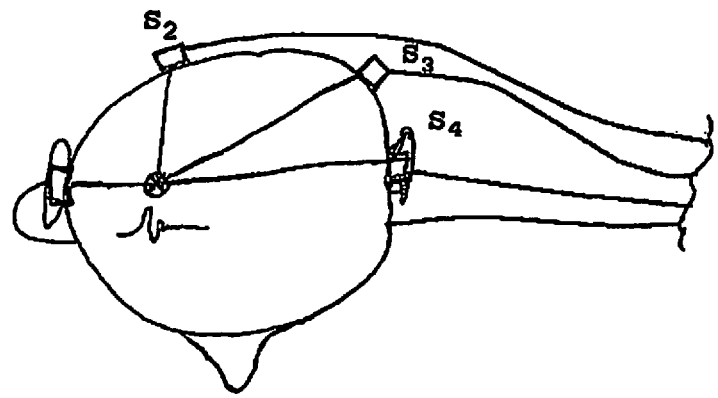
FIG. 19A is a plan view in one plane of four sensors on a human head with the distances from a noise source to each sensor.
Figure 19B:
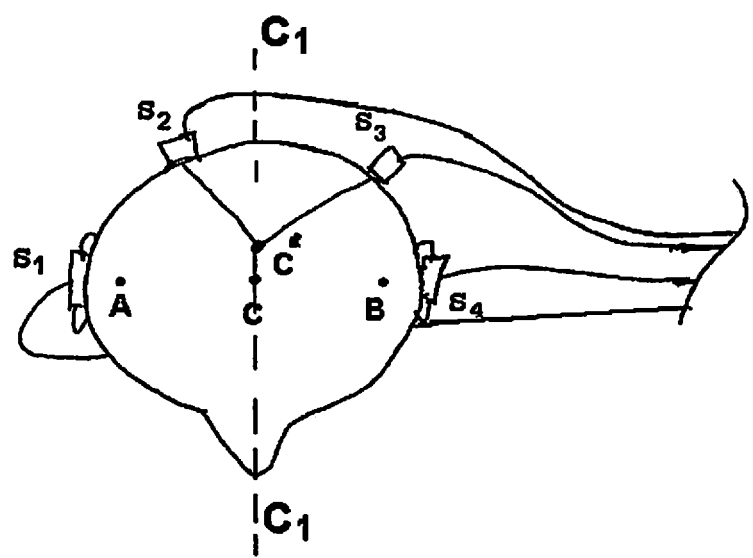
FIG. 19B is a plan view in one plane of four sensors on a human head with several possible sources of sound indicated.

FIG. 19A is a diagram of a patient with sensors $S_1$ through $S_4$ attached to the head. A signal source at X is located at distances $D_1$ through $D_4$ from the respective sensors. A waveform is shown at X depicting the acoustic signature that is emitted at location X. FIG. 19B is a diagram of a patient as in FIG. 19A. Four locations within the head of the patient are shown; points A, B C and C'. A centerline of symmetry is shown with point C' lying on the centerline and equal distance from sensors $S_2$ and $S_4$. Point C is also on the centerline and a short distance from point C'. Small changes in the distances $D_2$ and $D_3$ represent the small distance from C' to C. Beamforming techniques depend on changing the phase relationship between data collected by the sensors in a precise and controlled way, such as represented by the example in FIG. 19B.

Figures 20, 21:
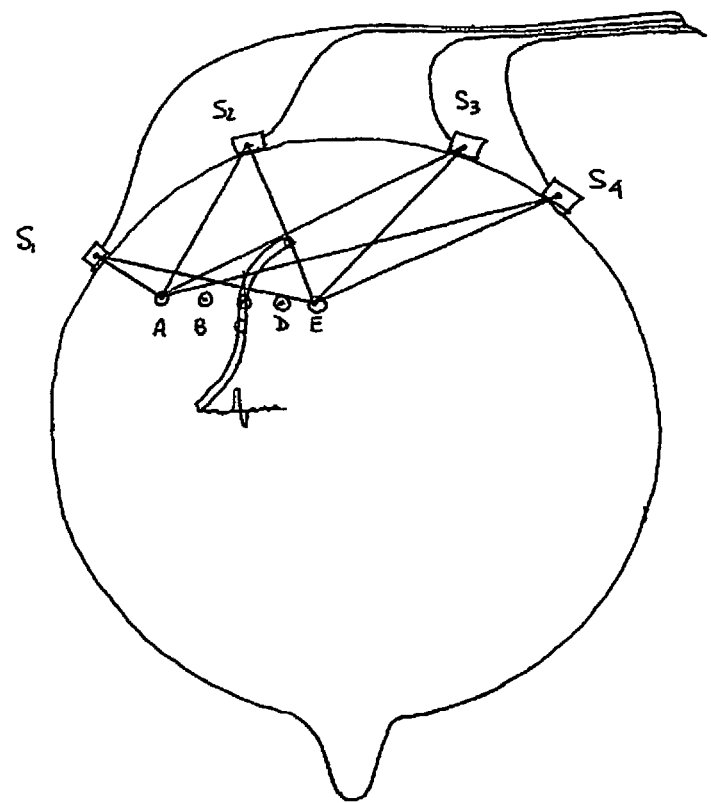
FIG. 20 is a plan view of the head with sensors shown and the geometry of beam forming.
FIG. 21 is a table giving the distances for four sensors and five beam forming position.
Figure 22:
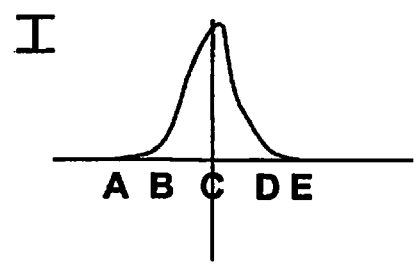
FIG. 22 is a plot of the width of a blood vessel determined by beam forming.
Figure 23:
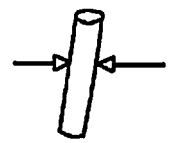
FIG. 23 is a diagram indicating the width of a blood vessel based on merging the NN output and the beam forming data.
Figure 24:
FIG. 24 is a figure of a patient being injected with ultrasound contrast agent.
Figure 25A:
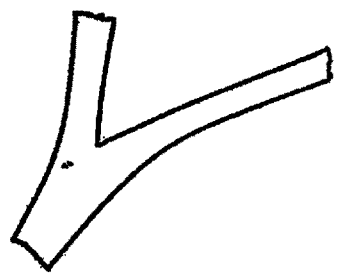
FIGS. 25A and 25B are figures of a branch in a blood vessel without and with ultrasound contrast.
Figure 25B:
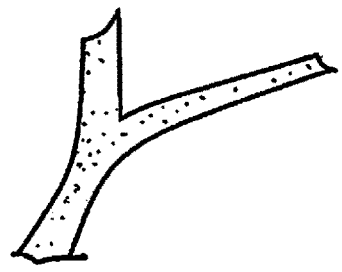
Figure 26:
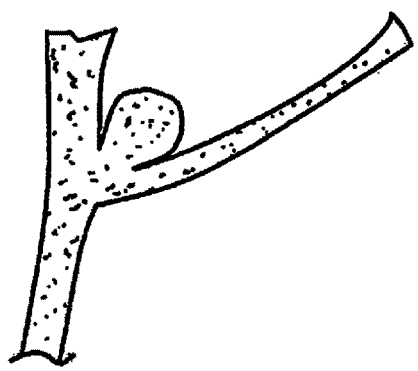
FIG. 26 is a figure of an aneurysm in the branch of a vessel as imaged with bursting bubbles.
Figure 27:
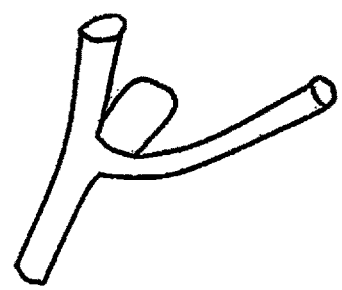
FIG. 27 is a figure of how an image of the vessel and aneurysm would be displayed after processing.
Figure 28:
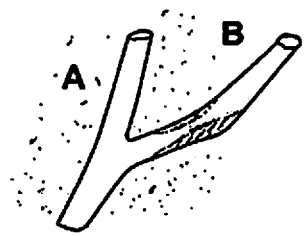
FIG. 28 is a figure of a branching vessel and areas of perfusion and non-perfusion.
Figure 29:
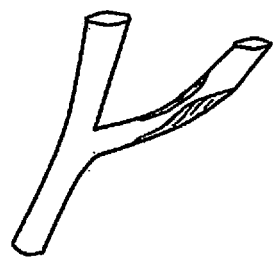
FIG. 29 is a figure of a vessel blocked by a stenosis.
Figure 30:
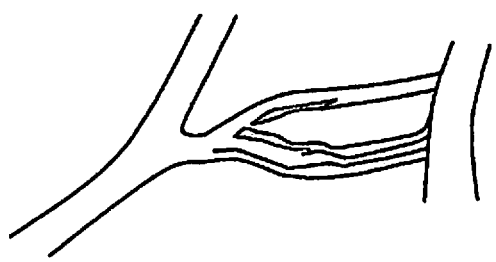
FIG. 30 is a figure of an AVM (arterial venous malformation).
Figure 31:
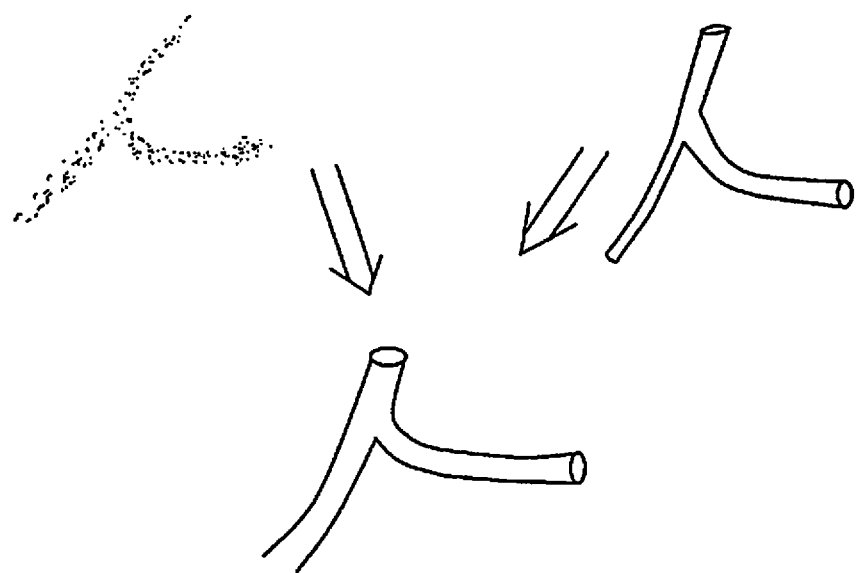
FIG. 31 is a diagram of how bursting bubbles combine with a NN image to produce an improved image.
Figure 32:
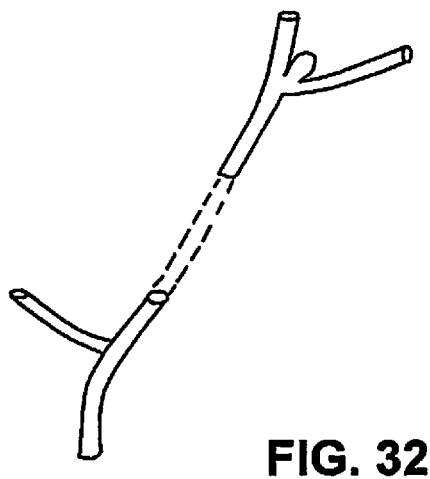
FIG. 32 is a figure that depicts how two segments derived from imaging can be connected by knowledge of the anatomy.
Figure 33:
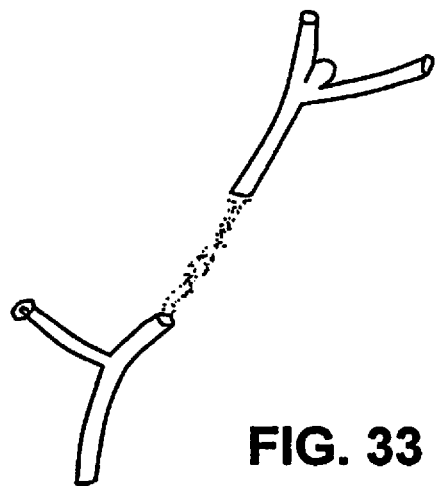
FIG. 33 is a figure that depicts how two segments derived from imaging can be connected by bursting bubble data.
Figure 34:
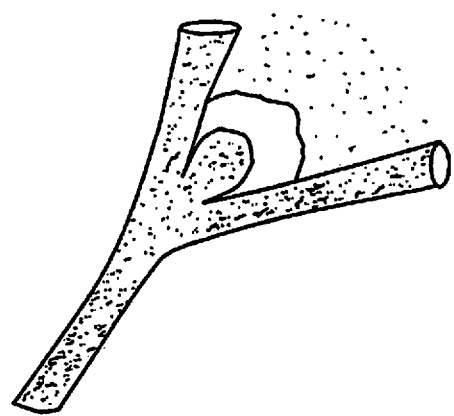
FIG. 34 is a figure that depicts an area of pooled blood in proximity to an aneurysm.

FIG. 20 shows a pictorial diagram of a patient with sensors $S_1$ through $S_4$ as is shown in FIG. 19A with the additional points A-E shown. Points A through E represent small steps across a point of interest, as depicted by a segment of vessel shown across the points A-E. The distances from each point A-E to each sensor S1-S4 are different and are shown in the table in FIG. 21.

An example would be when giving tPA to dissolve a clot. The clot region could be monitored and tPA administered while watching the blood flow and perfusion so that the right amount of tPA is administered. This would be possible even if the patient were not able to indicate physical improvements, i.e., asleep or in a natural or induced coma.

The preferred embodiments described above are intended to illustrate the principles of the invention, but not to limit its scope. Other embodiments and variations to these preferred embodiments will be apparent to those skilled in the art and may be made without departing from the spirit and scope of the invention as defined in the following claims.

The invention claimed is:

1. A system for non-invasive detection of abnormal cranial conditions, the system comprising:
   an array of accelerometers configured to externally engage a patient's head, wherein the array of accelerometers comprises four accelerometers configured to contact the patient's head at four different positions;
   wherein each of said four accelerometers is configured to measure acceleration of the patient's head at one of said four different positions resulting from displacement of the patient's skull at said one of said four different positions caused by heartbeat-induced pulsing of blood into cranial vasculature;
   wherein each of said four accelerometers is configured to generate signal data responsive to said acceleration of the patients head at one of said four different positions resulting from displacement of the patients skull at said one of said four different positions caused by heartbeat-induced pulsing of blood into cranial vasculature;
   a processing system connected to said four accelerometers, wherein said processing system is configured to
   receive said signal data from all of said four accelerometers simultaneously,
   analyze said signal data from all of said four accelerometers in parallel and perform in-phase and phase-shifted correlation of said signal data, and
   match said signal data with known signal data of abnormal cranial conditions to thereby detect abnormal cranial conditions of the patient non-invasively; and
   an image database configured to generate a display indicative of said abnormal cranial conditions of the patient.

2. The system of claim 1, wherein each of said four accelerometers has a sensitivity of at least 500 mV/g.

3. The system of claim 2, wherein said array of accelerometers comprises five accelerometers configured to contact the patient's head at five different positions.

4. The system of claim 1, wherein said processing system comprises:
   an analog to digital converter which converts said signal data from all of said four accelerometers into digital signal data; and
   a signal processing component which performs Fourier transform signal processing of said digital signal data.

5. The system of claim 4, further comprising:
   a conditions library; and
   a digital neural network which receives input from said conditions library and said signal processing block.

6. The system of claim 1, further comprising:
   wherein said processing system is configured to receive pulse timing information from a pulse sensor for use in analyzing said signal data from all of said four accelerometers.

7. The system of claim 1, further comprising:
   a pulse sensor which generates pulse timing information; and
   wherein said processing system is configured to receive pulse timing information from said pulse sensor for use in analyzing said signal data from all of said four accelerometers.

8. The system of claim 1, wherein said processing system is further configured to correlate said signal data from all of said four accelerometers.

9. The system of claim 1, wherein said processing system is configured to receive and process said signal data in parallel form all of said four accelerometers.

10. The system of claim 1, wherein said abnormal cranial conditions are abnormal cranial conditions selected from vasospasm and concussion.

11. A method for non-invasive detection of abnormal cranial conditions, the method comprising:
    providing an array of accelerometers comprising four accelerometers, and a processing system connected to said four accelerometers;
    engaging the array of accelerometers with a head of a patient externally such that the four accelerometers contact four different positions of the patients head;
    using the four accelerometers to measure acceleration of the patient's head at said four different positions resulting from displacement of the patient's skull at said four different positions caused by heartbeat-induced pulsing of blood into cranial vasculature;
    generating signal data responsive to said acceleration of the patients head said four different positions resulting from displacement of the patient's skull at said four different positions caused by heartbeat-induced pulsing of blood into cranial vasculature;

receiving said signal data at said processing system simultaneously;

analyzing said signal data in parallel with said processing system and performing in-phase and phase-shifted correlation of said signal data;

matching said signal data with known signal data of abnormal cranial conditions to thereby detect abnormal cranial conditions of the patient non-invasively; and generating a display indicative of said abnormal cranial conditions of the patient.

12. The method of claim 11, wherein each of said four accelerometers has a sensitivity of at least 500 mV/g.

13. The method of claim 11, wherein said array of accelerometers comprises five accelerometers configured to contact the patient's head at five different positions.

14. The method of claim 11, further comprising:
converting said signal data from all of said four accelerometers into digital signal data; and
performing Fourier transform signal processing of said digital signal data.

15. The method of claim 11, further comprising:
providing a conditions library comprising known signal data of abnormal cranial conditions.

16. The method of claim 11, further comprising:
receiving pulse timing information from a pulse sensor; and
using said pulse timing information in said analyzing said signal data with said processing system.

17. The method of claim 11, wherein analyzing said signal data with said processing system comprises correlating said signal data from all of said four accelerometers.

18. The method of claim 11, wherein said abnormal cranial conditions are abnormal cranial conditions selected from vasospasm and concussion.

19. A system for non-invasive detection of abnormal cranial conditions, the system comprising:
an array of accelerometers comprising four accelerometers;
wherein the array of accelerometers is configured to engage with a head of a patient externally such that the four accelerometers contact four different positions on the patient's head;
wherein said four accelerometers are configured to measure acceleration of the patients head at four different positions, and generate signal data responsive to said acceleration of the patients head said four different positions resulting from displacement of the patients skull at said four different positions caused by heartbeat-induced pulsing of blood into cranial vasculature;
a processing system connected to said four accelerometers, wherein said processing system is configured to,
receive simultaneously from said four accelerometers said signal data responsive to said acceleration of the patients head at said four different positions resulting from displacement of the patients skull at said four different positions caused by heartbeat-induced pulsing of blood into cranial vasculature;
analyze said signal data in parallel and perform in-phase and phase-shifted correlation of said signal data, and
match said signal data with known signal data of abnormal cranial conditions to thereby detect abnormal cranial conditions of the patient non-invasively; and
an image database configured to generate a display indicative of said abnormal cranial conditions of the patient.

20. The system of claim 19, wherein each of said four accelerometers has a sensitivity of at least 500 mV/g.

21. The system of claim 19, wherein said processing system comprises:
an amplifier connected to said four accelerometers and an analog to digital converter connected to said amplifier which converts said signal data from said four accelerometers into digital signal data.

22. The system of claim 19, wherein said processing system is configured to correlate said signal data from said four accelerometers.

23. The system of claim 19, wherein said processing system is configured to perform Fourier transform processing of said signal data from said four accelerometers.

* * * * *